United States Patent [19]

Speranza et al.

[11] 4,237,282

[45] Dec. 2, 1980

[54] UREA DERIVATIVE AND USE AS POLYURETHANE CATALYST

[75] Inventors: George P. Speranza; Robert L. Zimmerman, both of Austin, Tex.

[73] Assignee: Texaco Development Corporation, White Plains, N.Y.

[21] Appl. No.: 41,359

[22] Filed: May 22, 1979

Related U.S. Application Data

[62] Division of Ser. No. 952,027, Oct. 16, 1978.

[51] Int. Cl.³ .......................................... C07D 265/30
[52] U.S. Cl. .................................. 544/168; 521/129; 528/53
[58] Field of Search ........................................ 544/168

[56] References Cited

U.S. PATENT DOCUMENTS

| | | | |
|---|---|---|---|
| 2,850,529 | 9/1958 | Pinson | 544/162 |
| 3,234,153 | 2/1966 | Britain | 521/129 |
| 3,678,157 | 7/1972 | Kalopissis et al. | 544/162 |
| 4,012,445 | 3/1977 | Priest et al. | 521/129 |

Primary Examiner—Maurice J. Welsh
Attorney, Agent, or Firm—Carl G. Ries; Robert A. Kulason; James L. Bailey

[57] ABSTRACT

Covers N-(3-dimethylaminopropyl)-N'-(3-morpholinopropyl)urea. Also covers a method of producing a polyurethane by utilizing said above compound as a catalyst in reacting an organic polyisocyanate with an organic polyester polyol or polyether polyol in the presence of said catalyst.

1 Claim, No Drawings

UREA DERIVATIVE AND USE AS POLYURETHANE CATALYST

This is a division of application Ser. No. 952,027, filed Oct. 16, 1978.

BACKGROUND OF THE INVENTION

1. Field of the Invention

This invention pertains to the field of urethane catalysts. More particularly, this invention relates to the use of a certain area derivative as a urethane catalyst.

2. Description of the Prior Art

The use of a catalyst in preparing polyurethanes by the reaction of a polyisocyanate, a polyol and perhaps other ingredients is known. The catalyst is employed to promote at least two, and sometimes three major reactions that must proceed simultaneously and competitively at balanced rates during the process in order to provide polyurethanes with the desired physical characteristics. One reaction is a chain-extending isocyanate-hydroxyl reaction by which a hydroxyl-containing molecule is reacted with an isocyanate-containing molecule to form a urethane. This increases the viscosity of the mixture and provides a polyurethane containing secondary nitrogen atom in the urethane groups. A second reaction is a cross-linking isocyanate urethane reaction by which an isocyanate-containing molecule reacts with a urethane group containing a secondary nitrogen atom. The third reaction which may be involved is an isocyanate-water reaction by which an isocyanate-terminated molecule is extended and by which carbon dioxide is generated to blow or assist in the blowing of foam. This third reaction is not essential if an extraneous blowing agent, such as a halogenated, normally liquid hydrocarbon, carbon dioxide, etc., is employed, but is essential if all or even part of the gas for foam generation is to be generated by this in situ reaction (e.g. in the preparation of "one-shot" flexible polyurethane foams).

The reactions must proceed simultaneously at optimum balanced rates relative to each other in order to obtain a good foam structure. If carbon dioxide evolution is too rapid in comparison with chain extension, the foam will collapse. If the chain extension is too rapid in comparison with carbon dioxide evolution, foam rise will be restricted resulting in a high density foam with a high percentage of poorly defined cells. The foam will not be stable in the absence of adequate crosslinking.

It has long been known that tertiary amines are effective for catalyzing the second crosslinking reaction. Typical amines of this type are found in U.S. Pat. Nos. 4,007,140; 3,073,787; 3,234,153; 3,243,389 and 3,446,771. However, many amines of this class have a strong amine odor which is carried over to the polyurethane foam.

In still other cases, some tertiary amines impart a color to the product foam known as "pinking" and/or cause or fail to prevent undue foam shrinkage.

In addition to problems of odor, pinking, etc., other tertiary amines suffer still further deficiencies. For example, in some instances the compounds are relatively high in volatility leading to obvious safety problems. In addition, some catalysts of this type do not provide sufficient delay in foaming, which delay is particularly desirable in molding applications to allow sufficient time to situate the preform mix in the mold. Yet other catalysts, while meeting specifications in this area do not yield foams with a desirable tack-free time. In addition, some catalysts of this type are solids causing handling problems.

Lastly, in many cases blends of catalysts containing different tertiary amine groups must be utilized in order to achieve the desired balance between gelling and flowing of foams.

It would therefore be a substantial advance in the art if a new class of amine catalysts were discovered which overcome the just enumerated disadvantages of the prior art.

SUMMARY OF THE INVENTION

A new compound has been discovered which has been found useful as a polyurethane catalyst. This compound is N-(3-dimethylaminopropyl)-N'-(3-morpholinopropyl)urea.

DESCRIPTION OF THE PREFERRED EMBODIMENTS

The compound here may be prepared by resort to a wide variety of synthetic techniques. However, preferably urea is condensed with dimethylaminopropylamine until ammonia evolution ceases. Thereafter, this derivative is in turn condensed with aminopropylmorpholine until one again notes ceasage of ammonia evolution.

The compound here possess a number of useful characteristics making it exceptionally attractive as a polyurethane catalyst. For example, it has rapid catalytic activity in the polyurethane foam area. In addition, the compound here is also relatively non-volatile and possesses little, if any odor. Also, the compound does not cause excessive pinking, so often observed when other tertiary amine catalysts are employed, particularly when polyester polyols are used to make urethanes. The catalyst of the invention is particularly desirable in foaming urethanes in that it provides a sufficient delay in the foaming operation to aid in processing. Yet the catalyst also gives good foams with desirable tack-free times. This delay time is particularly desirable in molding applications to allow sufficient time to situate the prefoam mix in the mold. In addition, the compound is easily prepared as typically described above, and is relatively inexpensive.

It has also been noted that the compound described here in addition to being almost odor-free can be used to prepare foams such as polyester-based urethane foams without noting any substantial shrinkage in the foam so made. Lastly, since the molecule itself contains two different types of tertiary amine groups, it may be used as the sole catalyst source without resort to a blend of amine catalyst containing varying tertiary amine groups. Thus, the desired balance between foam gelling and flowing is obtained without resort to a catalyst blend, and a good reaction profile is obtained with sole use of the catalyst of the invention.

To prepare polyurethanes using the catalyst here, any aromatic polyisocyanate may be used. Typical aromatic polyisocyanates include m-phenylene diisocyanate, p-phenylene diisocyanate, polymethylene polyphenylisocyanate, 2,4-toluene diisocyanate, 2,6-tolulene diisocyanate, dianisidine diisocyanate, bitolylene diisocyanate, naphthalene-1,4-diisocyanate, xylylene-1,4-diisocyanate, xylylene-1,3-diisocyanate, bis(4-isocyanatophenyl)methane, bis(3-methyl-4-isocyanatophenyl)methane, bis(3-methyl-4-isocyanatophenyl)methane, and 4,4'-diphenylpropane diisocyanate.

Greatly preferred aromatic polyisocyanates used in the practice of the invention are 2,4- and 2,6-toluene diisocyanates and methylene-bridged polyphenyl polyisocyanate mixtures which have a functionality of from about 2 to about 4. These latter isocyanate compounds are generally produced by the phosgenation of corresponding methylene bridged polyphenyl polyamines, which are conventionally produced by the reaction of formaldehyde and primary aromatic amines, such as aniline, in the presence of hydrochloric acid and/or other acidic catalysts. Known processes for preparing polyamines and corresponding methylene-bridged polyphenyl polyisocyanates therefrom are described in the literature and in many patents, for example, U.S. Pat. Nos. 2,683,730; 2,950,263; 3,012,008; 3,344,162 and 3,362,979.

Most preferred methylene-bridged polyphenyl polyisocyanate mixtures used here contain about 20 to about 100 weight percent methylene diphenyldiisocyanate isomers, with the remainder being polymethylene polyphenyl diisocyanates having higher functionalities and higher molecular weights. Typical of these are polyphenyl polyisocyanate mixtures containing about 20 to 100 weight percent methylene diphenyldiisocyanate isomers, of which 20 to about 95 weight percent thereof is the 4,4'-isomer with the remainder being polymethylene polyphenyl polyisocyanates of higher molecular weight and functionality that have an average functionality of from about 2.1 to about 3.5. These isocyanate mixtures are known, commercially available materials and can be prepared by the process described in U.S. Pat. No. 3,362,979, issued Jan. 9, 1968 to Floyd E. Bentley.

The hydroxyl-containing polyol component which reacts with the isocyanate may suitably be a polyester polyol or a polyether polyol having a hydroxyl number ranging from about 700 to about 25, or lower. When it is desired to provide a flexible foam, the hydroxyl number if preferably in the range from about 25 to 60. For rigid foams, the hydroxyl number is preferably in the range from 350 to 700. Semirigid foams of a desired flexibility are provided when the hydroxyl number is intermediate to the ranges just given.

When the polyol is a polyester, it is preferable to use as the polyester, a resin having a relatively high hydroxyl valve and a relatively low acid value made from the reaction of a polycarboxylic acid with a polyhydric alcohol. The acid component of the polyester is preferably of the dibasic or polybasic type and is usually free of reactive unsaturation, such as ethylenic groups or acetylenic groups. The unsaturation, such as occurs in the rings of such aromatic acids as phthalic acid, terephthalic acid, isophthalic acid, or the like, is non-ethylenic and non-reactive. Thus, aromatic acids may be employed for the acid component. Aliphatic acids, such as succinic acid, adipic acid, sebabic acid, azelaic acid, etc., may also be employed and are preferred. The alcohol component for the polyester shoulf preferably contain a plurality of hydroxyl groups and is preferably an aliphatic alcohol, such as ethylene glycol, glycerol, pentaerthritol, trimethylolethane, trimethylolpropane, mannitol, sorbitol, or methyl glucoside. Mixtures of two or more of the above identified alcohols may be employed also if desired. When a flexbile urethane foam is desired, the polyol should preferably have an average functionality of from about 2 to about 4 and a molecular weight of from about 2,000 to about 6,000. For rigid foams, the functionality of the polyol component is preferably from about 4 to about 8.

When the hydroxyl-containing component is a polyether polyol for use in flexible polyurethane foam, the polyol may be an alkylene oxide adduct of a polyhydric alcohol with a functionality of from about 2 to about 4. The alkylene oxide may suitably be ethylene oxide, propylene oxide, or 1,2-butylene oxide, or a mixture of some or all of these. The polyol will suitable have a molecular weight within the range of from about 2,000 to about 7,000. For flexible polyether polyurethane foams, the alkylene oxide is preferably propylene oxide or a mixture of propylene oxide and ethylene oxide.

For rigid polyether polyurethane foams, the polyol should have a functionality of from about 4 to about 8 and a molecular weight of from about 300 to about 1,200. Polyols for rigid polyether polyurethane foams may be made in various ways including the addition of an alkylene oxide as above to a polyhydric alcohol with a functionality of from 4 to 8. These polyols may also be, for example, Mannich condensation products of a phenol, an alkanolamine, and formaldehyde, which Mannich condensation product is then reacted with an alkylene oxide (see U.S. Pat. No. 3,297,597).

The amount of hydroxyl-containing polyol compound to be used relative to the isocyanate compound in both polyester and polyether foams normally should be such that the isocyanate groups are present in at least an equivalent amount, and preferably, in slight excess, compared with the free hydroxyl groups. Preferably, the ingredients will be proportioned so as to provide from about 1.05 to about 1.5 mol equivalents of isocyanate groups per mole equivalent of hydroxyl groups. However, for certain shock absorbing foams we have found that by using the catalyst of our invention the mol equivalents of isocyanate to hydroxyl groups can be as low as 0.4.

When water is used, the amount of water, based on the hydroxyl compound, is suitably within the range of about 0.05 mol per mol equivalent of hydroxy compound.

It is within the scope of the present invention to utilize an extraneously added inert blowing agent such as a gas or gas-producing material. For example, halogenated low-boiling hydrocarbons, such as trichloromonofluoromethane and methylene chloride, carbon dioxide, nitrogen, etc., may be used. The inert blowing agent reduces the amount of excess isocyanate and water that is required in preparing flexible urethane foam. For a rigid foam, the use of water is often avoided and the extraneous blowing agent is used exclusively. Selection of the proper blowing agent is well within the knowledge of those skilled in the art. See for example U.S. Pat. No. 3,072,082.

The catalyst discovered here which is useful in the preparation of rigid or flexible polyester or polyether polyurethane foams, based on the combined weight of the hydroxyl-containing compound and polyisocyanate is employed in an amount of from about 0.05 to about 4.0 weight percent. More often, the amount of catalyst used is 0.1–1.0 weight percent. Most preferably, the catalyst here is employed to prepare flexible polyester or polyether polyurethane slab stock foams. However, as seen below, rigid foams may likewise be prepared without departing from the scope of the invention.

The catalyst of this invention may be used either alone or in a mixture with one or more other catalysts such as tertiary amines or with an organic tin compound or other polyurethane catalysts. However, as noted above resort to combination with other tertiary amines is generally not necessary. The organic tin compound, particularly useful in making flexible foams may suitably be a stannous or stannic compund, such as a stannous salt of a carboxylic acid, a trialkyltin oxide, a dialkyltin dihalide, a dialkyltin oxide, etc., wherein the organic groups of the organic portion of the tin compound are hydrocarbon groups containing from 1 to 8 carbon atoms. For example, dibutyltin dilaurate, dibutyltin diacetate, diethyltin diacetate, dihexyltin diacetate, di-2-ethylhexyltin oxide, dioctyltin dioxide, stannous octoate, stannous oleate, etc., or a mixture thereof, may be used.

Such other tertiary amines include trialkylamines (e.g. trimethylamine, triethylamine), heterocyclic amines, such as N-alkylmorpholines (e.g, N-methylmorpholine, N-ethylmorpholine, etc.), 1,4-dimethylpiperazine, triethylenediamine, etc., and aliphatic polyamines, such as N,N,N'N'-tetramethyl-1,3-butanediamine.

Conventional formulation ingredients are also employed, such as, for example, foam stabilizers, also known as silicone oils or emulsifiers. The foam stabilizer may be an organic silane or siloxane. For example, compounds may be used having the formula:

$$RSi[O-(R_2SiO)_n-(oxyalkylene)_mR]_3$$

wherein R is an alkyl group containing from 1 to 4 carbon atoms; n is an integer of from 4 to 8; m is an integer of from 20 to 40; and the oxyalkylene groups are derived from propylene oxide and ethylene oxide. See, for example, U.S. Pat. No. 3,194,773.

In preparing a flexible foam, the ingredients may be simultaneously, intimately mixed with each other by the so-called "one-shot" method to provide a foam by a one-step process. In this instance, water should comprise at least a part (e.g., 10% to 100%) of the blowing agent. The foregoing methods are known to those skilled in the art, as evidenced by the following publication: duPont Foam Bulletin, "Evaluation of Some Polyols in One-Shot Resilient Foams", Mar. 22, 1960.

When it is desired to prepare rigid foams, the "one-shot" method or the so-called "quasi-prepolymer method" is employed, wherein the hydroxyl-containing component preferably contains from about 4 to 8 reactive hydroxyl groups, on the average, per molecule.

In accordance with the "quasi-prepolymer method", a portion of the hydroxyl-containing component is reacted in the absence of a catalyst with the polyisocyanate component in proportions so as to provide from about 20 percent to about 40 percent of free isocyanato groups in the reaction product, based on the polyol. To prepare a foam, the remaining portion of the polyol is added and the two components are allowed to react in the presence of catalytic systems such as those discussed above and other appropriate additives, such as blowing agents, foam stabilizing agents, fire retardants, etc. The blowing agent (e.g., a halogenated lower aliphatic hydrocarbon), the foam-stabilizing agent, the fire retardant, etc., may be added to either the prepolymer or remaining polyol, or both, prior to the mixing of the component, whereby at the end of the reaction a rigid polyurethane foam is provided.

Urethane elasomers and coatings may be prepared also by known techniques in accordance with the present invention wherein a tertiary amine of this invention is used as a catalyst. See, for example, duPont Bulletin PB-2, by Remington and Lorenz, entitled "The Chemistry of Urethane Coatings".

The invention will be illustrated further with respect to the following specific examples, which are given by way of illustration and not as limitations on the scope of this invention.

EXAMPLE I

Preparation of the Catalyst

In a 500 ml flask equipped with a mechanical stirrer, thermometer, reflux condensor and an addition funnel was placed 54 grams of urea and 91.8 grams of dimethylaminopropylamine. The mixture was heated to 120° C. and held for 2 hours. At this time the ammonia evolution had stopped. Then 135 grams of aminopropylmorpholine was added and the contents heated to 180° C. The reaction mixture was held at 180° C. for 2 hours. At this time ammonia evolution had stopped. The reaction mass was cooled and poured out. The product was identified by NMR and IR. It was also shown not to be bis(dimethylaminopropyl)urea or bis(morpholinopropyl)urea by gel permeation chromatography.

EXAMPLES II-VI

The following gives typical foam formulations and reaction profiles using the catalyst here to prepare polyester-based urethane foams. Example II should be compared with Example V. Most unexpectedly the compound of the invention provided excellent foams (Example II) versus a combination of ureas each containing one of the tertiary amine groups, both of which are carried by the catalyst here. As seen in Example V, foam shrinkage occurred and coarse cells were noted when the combined ureas were used as a catalyst source.

TABLE I

|  | II | III | IV | V | VI |
|---|---|---|---|---|---|
| FOMREZ ® 50[1] | 100 | 100 | 100 | 100 | 100 |
| Silicone L-532[2] | 1.0 | 1.0 | 1.0 | 1.0 | 1.0 |
| Water | 3.6 | 3.6 | 3.6 | 3.6 | 3.6 |
| N-(3-dimethylaminopropyl)-N'-(3-morpholinopropyl)urea | 1.25 | — | — | — | 0.75 |
| N,N'bis(3-dimethylaminopropyl)urea | — | 0.75 | — | 0.625 | — |
| N,N'-bis(3-morpholinopropyl)urea | — | — | 2.0 | 0.625 | — |
| Palmityl dimethylamine | 0.1 | 0.1 | 0.1 | 0.1 | 0.1 |
| THANCAT ® DD[3] | — | — | — | — | 0.125 |
| Toluene diisocyanate (80/20 isomer distribution) | 43.5 | 43.5 | 43.5 | 43.5 | 43.5 |
| Cream time (seconds) | 10 | 10 | 12 | 9 | 10 |
| Rise time (seconds) | 78 | 75 | 120 | 72 | 80 |
| Appearance | No shrinkage Slightly pale yellow | Slight shrinkage Coarse cells | Collapsed Was orange | Slight shrinkage Off White | Good foam White |

TABLE I-continued

|  | II | III | IV | V | VI |
|---|---|---|---|---|---|
|  | Fine cells | Not a good foam | pink in color | Coarse cells | Fine cells |

[1] A polyester made from adipic acid, trimethylolpropane and diethylene glycol of approximately 2000 molecular weight available from Witco Chemical Co.
[2] A silicone product of Union Carbide Corp.
[3] A product of Jefferson Chemical Company, Inc. (dimethylaminoethyl dimethylaminopropyl ether).

EXAMPLE VII

The following demonstrates the use of the catalyst of the invention in a polyether-based flexible urethane foam.

| | |
|---|---|
| THANOL® F-3016[1] | 100 |
| Silicone L-520[2] | 1.0 |
| Water | 4.0 |
| 50% Stannous octoate in dioctylphthalate | 0.5 |
| Catalyst Example I | 0.3 |
| Toluene diisocyanate (80/20 isomer distribution) | 51.6 |
| Cream time (seconds) | 12 |
| Rise time (seconds) | 90 |

[1] A product of Jefferson Chemical Co., Inc., a propoxylated and ethoxylated glycerin.
[2] A hydrolyzable silicone surfactant sold by Union Carbide Corp.

EXAMPLE VIII

The following demonstrate the use of the catalyst here in a rigid polyurethane foam.

| | |
|---|---|
| THANOL® RS-700[1] | 36.3 |
| Silicone DC-193[2] | 0.5 |
| Trichlorofluoromethane | 14 |
| Catalyst Example I | 0.4 |
| Dibutyltin dilaurate | 0.08 |
| Mondur MR[3] | 48.7 |
| Cream time (seconds) | 20 |
| Tack free time (seconds) | 55 |
| Rise time (seconds) | 55 |

[1] Propoxylated sorbitol with a molecular weight about 700 from Jefferson Chemical Co., Inc.
[2] A silicone surfactant sold by Dow-Corning.
[3] A polymeric isocyanate available from Mobay Chemical Co. It has a functionality of about 2.7.

We claim:
1. N-(3-dimethylaminopropyl)-N'-(3-morpholinopropyl)urea.

* * * * *